United States Patent [19]
Andersson et al.

[11] Patent Number: 5,165,404
[45] Date of Patent: Nov. 24, 1992

[54] BIOLOGICAL TISSUE STIMULATION DEVICE WITH CONTROL MEANS FOR DETERMINING STIMULATION SENSITIVITY CALCULATION TIMING

[75] Inventors: Peter Andersson, Stockholm; Bo Köpsén, Bàlsta, both of Sweden

[73] Assignee: Siemens Aktiengesellschaft, Munich, Fed. Rep. of Germany

[21] Appl. No.: 685,128

[22] Filed: Apr. 12, 1991

[30] Foreign Application Priority Data

Apr. 24, 1990 [EP] European Pat. Off. ........ 90107693.5

[51] Int. Cl.⁵ .................... A61N 1/365; A61N 1/08
[52] U.S. Cl. ............................ 128/419 PG; 128/421; 128/419 PT
[58] Field of Search ............... 128/419 PG, 419 PT, 128/421

[56] References Cited

U.S. PATENT DOCUMENTS

| | | | |
|---|---|---|---|
| 3,757,792 | 9/1973 | Mulier et al. | 128/419 P |
| 4,402,322 | 9/1983 | Duggan | 128/419 PG |
| 4,729,376 | 3/1988 | DeCote, Jr. | 128/419 PT |
| 4,878,497 | 11/1989 | Callaghan et al. | 128/419 PG |
| 4,955,376 | 9/1990 | Callaghan et al. | 128/419 PG |
| 4,969,460 | 11/1990 | Callaghan et al. | 128/419 PG |
| 4,969,461 | 11/1990 | Callaghan et al. | 128/419 PG |
| 4,969,462 | 11/1990 | Callaghan et al. | 128/419 PG |
| 4,969,464 | 11/1990 | Callaghan et al. | 128/419 PG |
| 4,969,467 | 11/1990 | Callaghan et al. | 128/419 PG |
| 4,979,507 | 12/1990 | Heinz et al. | 128/419 PG |

FOREIGN PATENT DOCUMENTS

| | | |
|---|---|---|
| 0236562 | 9/1987 | European Pat. Off. |
| 2342030 | 3/1975 | Fed. Rep. of Germany |
| 2619001 | 11/1977 | Fed. Rep. of Germany |

*Primary Examiner*—Kyle L. Howell
*Assistant Examiner*—Kennedy J. Schaetzle
*Attorney, Agent, or Firm*—Hill, Van Santen, Steadman & Simpson

[57] ABSTRACT

A device for biological tissue stimulation continually undertakes an evaluation of the stimulation sensitivity of the biological tissue to be stimulated, so that the stimulation energy can be set at a level just high enough to evoke a tissue response. Each evaluation ensues by stimulating the tissue with progressively lower energy levels, until no tissue response is detected. In order to improve matching of the stimulation energy to the varying stimulation sensitivity, and to keep the number of unsuccessful stimulation attempts, which occur during each evaluation, low, a device is disclosed wherein calculation of the stimulation sensitivity occurs at periodic time intervals, each time interval having a duration which is selected dependent on the variation in the stimulation sensitivity between the two most recently occurring calculations of the stimulation sensitivity. The device may be, for example, a heart pacemaker. A method for tissue stimulation is also disclosed.

10 Claims, 3 Drawing Sheets

BIOLOGICAL TISSUE STIMULATION DEVICE WITH CONTROL MEANS FOR DETERMINING STIMULATION SENSITIVITY CALCULATION TIMING

BACKGROUND OF THE INVENTION

1. Field of the Invention

The present invention is directed to a device for biological tissue stimulation, in particular an implantable device such as a heart pacemaker.

2. Description of the Prior Art

Implantable devices for biological tissue stimulation are known which include a stimulation pulse generator which generates the stimulation pulses, and a detector which determines the reaction of the tissue to the stimulation pulse. A control unit is included which controls the stimulation pulse generator and which identifies the stimulation sensitivity of the tissue. The control unit sets the energy level of the stimulation pulses at a level just high enough to evoke a reaction in the stimulated tissue, by continually reducing the energy of the stimulation pulses, starting from a value lying above the stimulation sensitivity, until there is no reaction of the tissue to a stimulation pulse.

A device of this type is described in German AS 22 54 928, corresponding to U.S. Pat. No. 3,757,792, in the context of a heart pacemaker by which the heart of a patient is stimulated by the stimulation pulses. It is known that a contraction of the heart muscle, as a reaction of the heart to a stimulation pulse, occurs only when the energy of the stimulation pulse exceeds a defined stimulation sensitivity, or stimulation threshold, of the heart tissue. This stimulation sensitivity will vary from patient to patient. To maintain the energy consumption of the heart pacemaker low, instead of using a stimulation energy at a level which is a fixed, constant value above the current stimulation sensitivity, the energy of successive stimulation pulses is reduced in steps, and the reaction or response of the heart to each stimulation pulse is monitored. When no reaction occurs, the stimulation energy is then increased to a value known to lie above the stimulation sensitivity of the heart, and the same procedure is repeated. A matching of the stimulation energy, and thus of the energy consumption within the heart pacemaker, is thereby accomplished relative to the variable stimulation sensitivity of the heart.

In a similar arrangement for cardiac stimulation disclosed in European Application 0 236 562, the stimulation energy following the detection of a tissue reaction after a stimulation pulse is always diminished by a defined value, whenever a cardiac reaction was detected after each of the two immediately preceding stimulation events. If no heart reaction is detected to the current stimulation pulse, the heart is stimulated with a stimulation pulse having maximum energy, and the next stimulation pulse has an energy content increased by a defined amount in comparison to the energy of the unsuccessful stimulation pulse.

SUMMARY OF THE INVENTION

It is an object of the present invention to provide a device for biological tissue stimulation wherein the energy output of the device is matched to the variation curve of the stimulation sensitivity of the tissue, and additionally wherein the patient is not continually placed in discomfort due to unsuccessful stimulations as a consequence of the periodic downward transgression of the stimulation sensitivity.

The above object is achieved in accordance with the principles of the present invention in a device for biological tissue stimulation wherein a control unit implements the calculation of the stimulation sensitivity at periodic time intervals, with the time interval between a current calculation of this stimulation sensitivity and the next calculation is selected dependent on the difference between the currently identified value of the stimulation sensitivity and the previously identified value of the stimulation sensitivity. The time interval is shortened with increasing difference and is lengthened with decreasing difference.

An important advantage of the device disclosed herein is that the calculation of the stimulation sensitivity does not take place constantly, but only at defined time intervals whose length varies dependent on the modification in the stimulation sensitivity which has occurred, so that this stimulation sensitivity is re-calculated at longer time intervals if only small changes in the stimulation sensitivity are present, thereby placing a correspondingly lower stress on the patient, whereas the time interval between successive calculations of the stimulation sensitivity is shortened in the presence of larger changes in the stimulation sensitivity, to better follow those changes. The stress on the patient due to unsuccessful stimulation attempts, as occur for each individual calculating event, is significantly reduced.

The difference between the current value of the stimulation sensitivity and the previously calculated value of the stimulation sensitivity, which is used to select the length of the time interval, is preferably standardized or normalized in the control unit to the time interval between these two calculating events. As a result, the time interval between successive calculation events is matched to the variation of the stimulation sensitivity of the tissue to be stimulated per time unit, i.e., to the rate of change.

To insure a reliable stimulation of the tissue without unsuccessful stimulation attempts between the individual calculating events, the stimulation pulse generator in the device disclosed herein generates stimulation pulses after each calculation of the stimulation sensitivity, until the next calculation thereof, at an energy corresponding to the currently identified value of the stimulation sensitivity, plus a safety margin. This safety margin has a magnitude, for the duration until the next calculation of the stimulation sensitivity, such that the energy of the generated stimulation pulses will always be above the stimulation sensitivity of the tissue, given an increase in the stimulation sensitivity during the interval.

In a further embodiment of the invention the stimulation pulse generator generates biphasic stimulation pulses for the calculation of the stimulation sensitivity, and subsequently generates monophasic stimulation pulses until the next calculation of the stimulation sensitivity. As used herein, the term "biphasic stimulation pulses" means, consistent with the teachings of German OS 23 42 030 and German OS 26 19 001, that the polarization phenomena produced in the tissue due to the stimulation pulse disappear so rapidly that a reliable acquisition of the reaction of the tissue to the stimulation is possible. The energy consumption of such biphasic pulses, however, is relatively high in comparison to monophasic pulses. Because, however, the device disclosed herein does not constantly generate the biphasic stimulation pulses, but only generates those pulses at defined time intervals for calculating the stimulation sensitivity of the tissue, whereas the tissue is excited in the meantime with monophasic pulses, the energy requirement for stimulation is still low.

The biphasic stimulation pulses preferably each comprise two sub-pulses of opposite polarity and the same energy, with a pause therebetween.

The above objects are also achieved in a method operating in accordance with the principles of the present invention.

DESCRIPTION OF THE PREFERRED EMBODIMENTS

Figure 1:
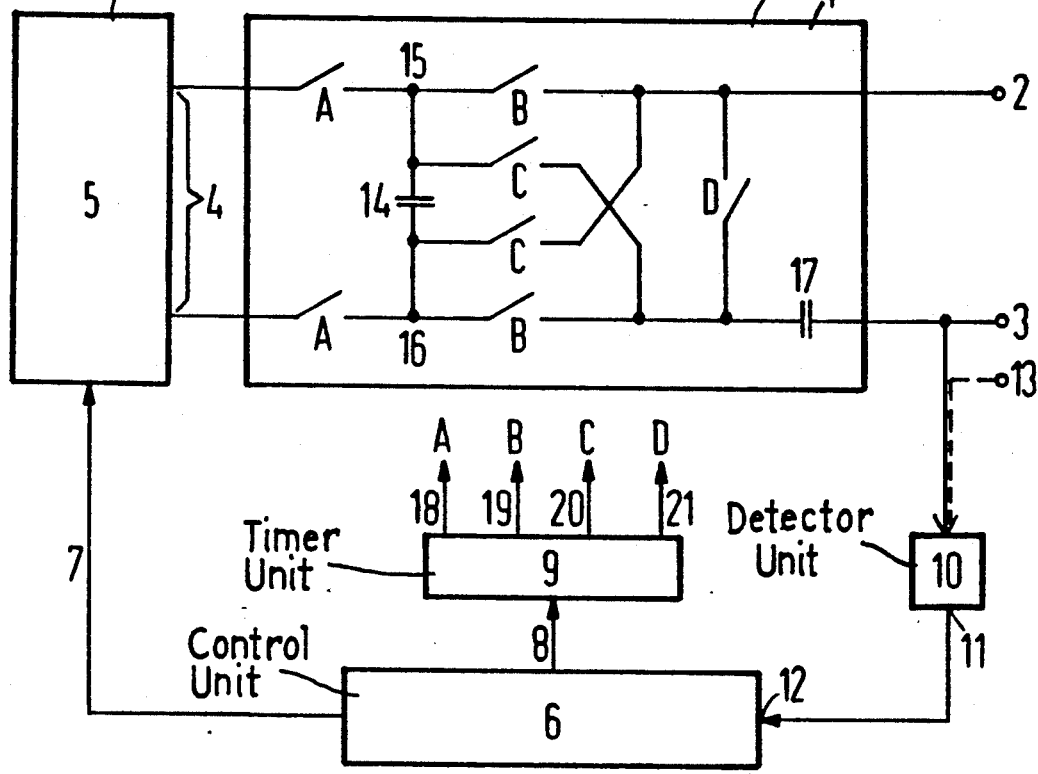
FIG. 1 is a schematic block diagram of an exemplary embodiment of a device for biological tissue stimulation constructed in accordance with the principles of the present invention.

As an exemplary embodiment for a device for biological tissue stimulation constructed in accordance with the principles of the present invention, FIG. 1 shows a block circuit diagram of a heart pacemaker for tissue stimulation. The heart pacemaker contains a stimulation pulse generator 1, having an output side to which a neutral electrode 2 and a stimulation electrode 3 are connected. The neutral electrode 2 is formed by the housing (not shown) of the heart pacemaker, whereas the stimulation electrode 3 is placed in the heart. The input side of the stimulation pulse generator 1 is connected to the output 4 of a stimulation voltage generator 5, which supplies the stimulation pulse generator 1 with predetermined voltage for the stimulation pulses to be generated. The value for this voltage is prescribed by a control unit 6, which is connected to the stimulation voltage generator 5 via a control line 7. The control unit 6 is also connected via a further control line 8 at its output side to a timer unit 9. As described in more detail below, the timer unit 9 controls the chronological course of the generation of the stimulation pulses in the stimulation pulse generator 1.

The stimulation electrode 3 is connected to a detector 10, which determines the reaction of the stimulated tissue following a stimulation pulse. An output 11 of the detector 10 is connected to a control input 12 of the control unit 6. Instead of being connected to the stimulation electrode 3, the detector 10 may alternatively be connected to a measuring electrode 13, arranged in proximity to the stimulation electrode 3, as indicated in dashed lines in FIG. 1.

A storage capacitor 14 is disposed in the stimulation pulse generator 1. The capacitor 14 has terminals 15 and 16 connected via a first switch pair A to the output 4 of the stimulation voltage generator 5. Via a second switch pair B and a third switch pair C, which are arranged in a bridge circuit, the capacitor 14 is also connected to the neutral electrode 2, and is also connected to the stimulation electrode 3 via an output capacitor 17. If the switch pair B is closed, the terminal 15 of the capacitor 14 will connected to the neutral electrode 2, and has the terminal 16 will connected to the output capacitor 17. If the switch pair C is closed, the terminal 16 will be connected to the neutral electrode 2 and the terminal 15 will be connected to the output capacitor 17. Lastly, a switch D is provided which connects the stimulation electrode 3 to the neutral electrode 2 via the output capacitor 17. The switch pairs A, B and C and the switch D are individually driven by the timer unit 9 via respective control lines 18, 19, 20 and 21, as described in detail below with respect to FIG. 2.

Figure 2:
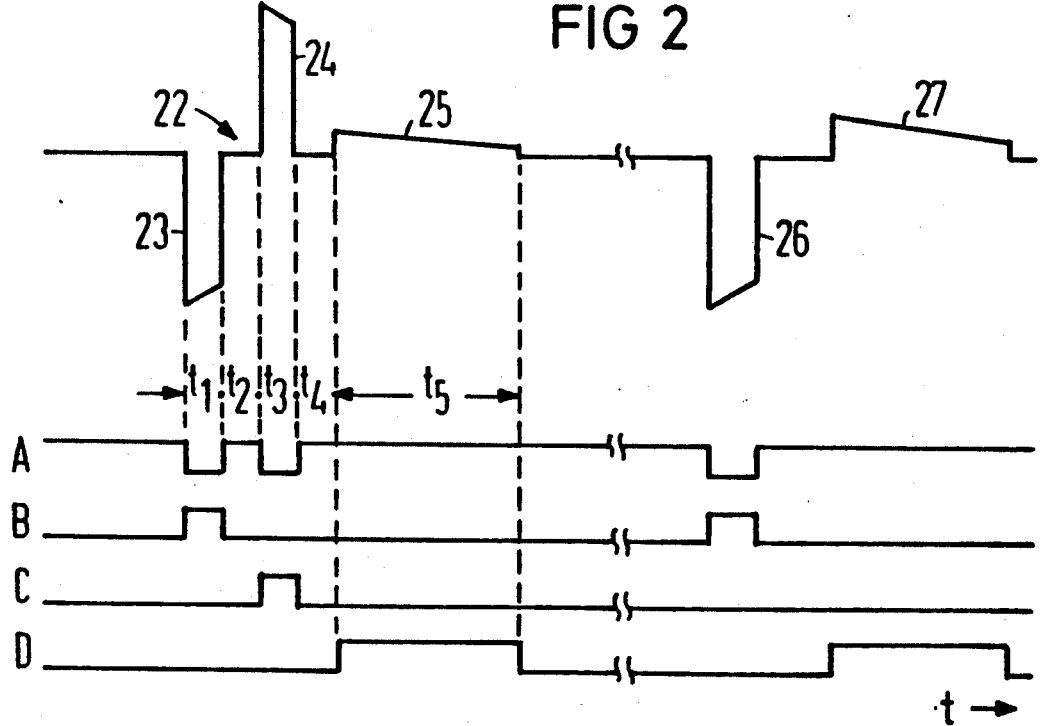
FIG. 2 is a time diagram showing different stimulation pulses, and the control signals for generating the pulses, as occur in the device of FIG. 1.

The time diagram of FIG. 2 shows an example of a biphasic stimulation pulse 22, which consists of a negative sub-pulse 23 followed by a positive sub-pulse 24, and a rapid discharge pulse 25. FIG. 2 also shows a monophasic stimulation pulse 26 and the respective control signals generated by the timer unit 9 for the switch pairs A, B and C and for the switch D, used to generate the stimulation pulses 22 and 26. A signal state deviating from zero indicates that the allocated switch is closed.

As long as the switch pair A is closed, the storage capacitor 14 is charged to the output voltage prescribed by the control unit 6 and generated by the stimulation voltage generator 5. For generating the biphasic stimulation pulse between the neutral electrode 2 and the stimulation electrode 3, the switch pair B is first closed for a duration $t_1$ and, following a pause of duration $t_2$, the switch pair C is closed for a duration $t_3$. Following a further pause of duration $t_4$, the switch D is closed for a duration $t_5$, as a result of which the output capacitor 17 is rapidly discharged. The polarization phenomena produced in the tissue in the region of the stimulation electrode 3 as a result of the stimulation are so rapidly dismantled with the biphasic stimulation signal 22 that a reliable determination of the reaction of the tissue, i.e., a determination substantially free of superimpositions of signals due to the polarization phenomena, to the biphasic stimulation is possible with the detector 10. If the reaction of the stimulated tissue is determined via the measuring electrode 13 adjacent to the stimulation electrode 3, the monophasic stimulation pulse 23, which is simpler to generate, can be employed for tissue stimulation instead of the biphasic stimulation pulse 22. The reason for this is that the action potential in the tissue proceeds to the measuring electrode 13 from the stimulation electrode 2 with a time delay, so that the polarization phenomena have substantially decayed during this time.

The monophasic stimulation pulse 26 is generated by closing the switch pair B. Subsequently, the output capacitor 17 is discharged by closing the switch D with a rapid discharge pulse 27. As shown in FIG. 2, the energy content of the monophasic stimulation pulse 26 is reduced by about half compared to that of the biphasic stimulation pulse 22, given the same amplitude. Despite their different energy content, both stimulation pulses 22 and 26 have approximately the same effect in the tissue stimulation. The reason for this is that the stimulation sensitivity of the tissue is dependent not only on the actual energy content of the stimulation pulse, but also on its shape. When stimulation energy is mentioned below with respect to the stimulation sensitivity of the tissue, the two different stimulation pulses are therefore considered equal in energy as long as they have the same effect on tissue stimulation.

Figure 3:
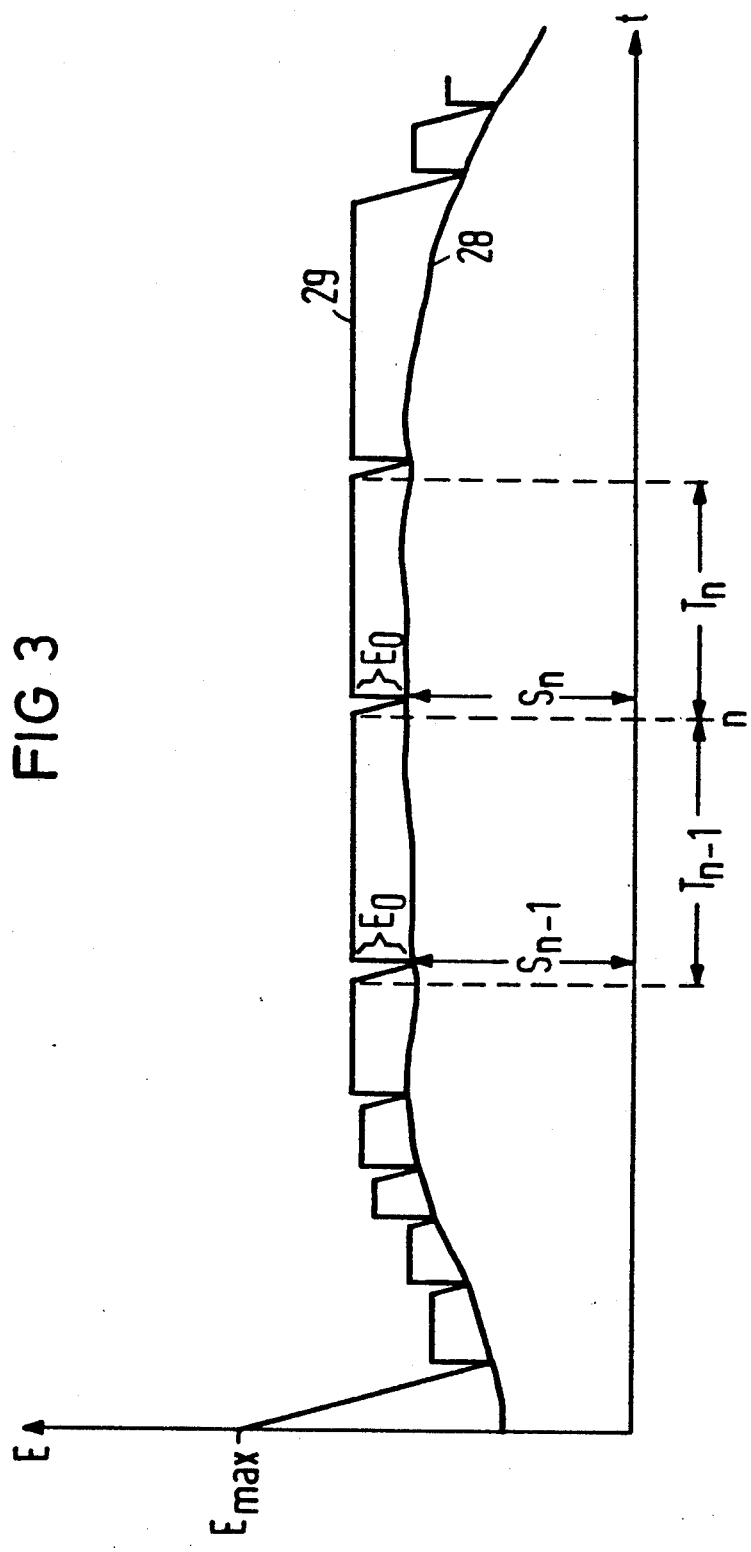
FIG. 3 is an example of the chronological curve of the stimulation sensitivity of tissue to be stimulated, and a curve of the stimulation energy adapted thereto achieved by the device of FIG. 1.
Figure 4:
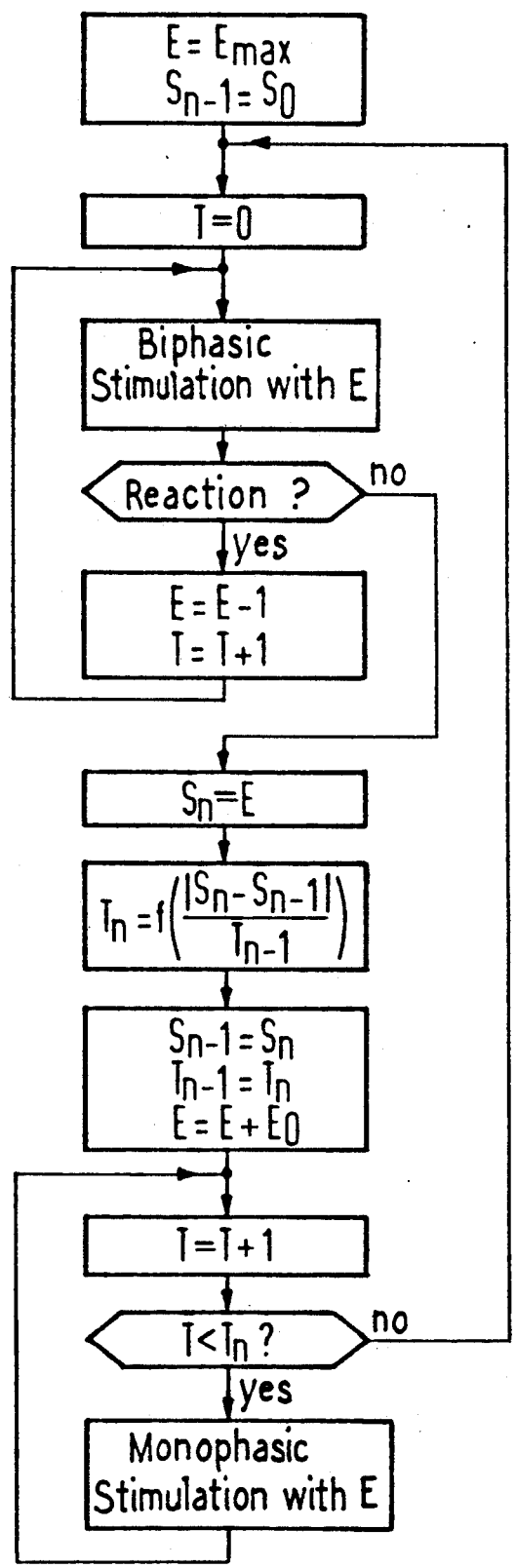
FIG. 4 is a flow chart showing individual method steps for explaining the operation of the device of FIG. 1.

Curve 28 in FIG. 3 shows a possible curve for the stimulation sensitivity of the tissue to be stimulated, dependent on time t. The stimulation sensitivity is expressed by an energy value E which a stimulation pulse must have, at a minimum, for a successful stimulation of the tissue. To assure successful stimulation at any time, the tissue could be constantly stimulated with a maximum energy $E_{max}$. In this case, however, the energy consumption would be extremely high. As set forth below, the stimulation energy is therefore adapted to the varying stimulation sensitivity of the tissue in accordance with the path of the curve referenced 29, and the method steps set forth in the flow chart of FIG. 4.

The stimulation sensitivity of the tissue is identified at a time n in FIG. 3. A value $S_{n-1}$ was most recently calculated for the stimulation sensitivity preceding a time interval $T_{n-1}$. Until the time n, the tissue was subsequently excited with a stimulation energy (curve 29) which lies above the calculated stimulation sensitivity $S_{n-1}$ by a safety margin $E_0$. For again calculating the stimulation sensitivity, a timer T (FIG. 4) is reset to zero. Subsequently, the tissue is charged with the biphasic stimulation pulse 22 (FIG. 2) at the most recently employed stimulation energy $E=S_{n-1}+E_0$, and immediately thereupon the reaction of the tissue is monitored by the detector 10. When a reaction of the stimulated tissue is detected, the stimulation energy E is diminished by an energy step, the timer T is incremented, and another biphasic stimulation pulse 22, with a diminished stimulation energy E, is generated after a stimulation time interval, which is not referenced in FIG. 4. This procedure is repeated until a reaction of the tissue does not occur, because the current stimulation sensitivity $S_n$ was downwardly transgressed. The change in energy of the biphasic stimulation pulse 22 can ensue by varying the pulse duration and/or the pulse amplitude. Depending on the difference between the current stimulation sensitivity $S_n$ just detected, and the stimulation sensitivity $S_{n-1}$ calculated most recently therebefore (with the time interval $T_{n-1}$ between the two calculating events), a new time interval $T_n$ is defined from the beginning of the current calculation until the next calculation of the stimulation sensitivity. Subsequently, the tissue is excited with the monophasic stimulation pulses 26 (FIG. 2) at a stimulation energy $E=S_n+E_0$ which lies above the calculated stimulation sensitivity $S_n$ by the safety margin $E_0$, until the timer T which is incremented after each stimulation, indicates the expiration of the time interval $T_n$. Subsequently, the stimulation sensitivity of the tissue is re-calculated as set forth above.

A biphasic stimulation pulse 22 can be generated periodically during the monophasic stimulation, for example after each tenth stimulation pulse, and the detector 10 can check whether the stimulation energy is still adequate for tissue stimulation. If this is not the case, the stimulation energy is increased. If the detector 10 is connected to the measuring electrode 13, the check for adequate stimulation energy given monophasic stimulation can continuously occur after each stimulation pulse 26.

The stimulation energy 29 is matched to the stimulation sensitivity 28 with the device disclosed herein, with the stress on the patient due to absent stimulation pulses being as low as possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for stimulating biological tissue comprising:
    pulse generator means for generating stimulation pulses;
    electrode means connected to said pulse generator means and adapted for electrical contact with said tissue for delivering said stimulation pulses to said tissue;
    detector means connected to said electrode means for monitoring the reaction of said tissue to a stimulation pulse; and
    control means connected to said pulse generator means and to said detector means for identifying the stimulation sensitivity of said tissue by progressively lowering the energy of successive stimulation pulses, starting from an energy value above said stimulation sensitivity, until no reaction of said tissue is detected by said detector means, said control means including means for calculating said stimulation sensitivity at periodic time intervals, and means for selecting a time interval between a current calculation of the stimulation sensitivity and a next calculation of the stimulation sensitivity dependent on the difference between a currently calculated value of said stimulation sensitivity and an immediately preceding calculated value of said stimulation sensitivity by shortening said time interval as said difference increases and lengthening said time interval as said difference decreases.

2. A device as claimed in claim 1 wherein said control means includes means for normalizing said difference to the time between said currently calculated value of said stimulation sensitivity and said immediately preceding calculated value of said stimulation sensitivity.

3. A device as claimed in claim 1 wherein said control means includes means for controlling said pulse generator means so that said pulse generator means generates stimulation pulses after each calculation of said stimulation sensitivity until a next calculation of said stimulation sensitivity with said stimulation pulses having an energy corresponding to said currently calculated value of said stimulation sensitivity, plus a safety margin.

4. A device as claimed in claim 1 wherein said pulse generator means includes means for generating biphasic stimulation pulses for calculation of said stimulation sensitivity and means for generating monophasic stimulation pulses between each calculation of said stimulation sensitivity.

5. A device as claimed in claim 4 wherein said means for generating said biphasic stimulation pulses is a means for generating two sub-pulses of opposite polarity and the same energy, with a pause between said two sub-pulses.

6. A method for stimulating biological tissue comprising:
    delivering a plurality of stimulation pulses to biological tissue;
    monitoring said biological tissue to determine the presence of a reaction of said tissue to a stimulation pulse;
    for identifying the stimulation sensitivity of said tissue, progressively lowering the energy of successive stimulation pulses, starting from an energy value above said stimulation sensitivity, until no reaction of said tissue is detected;

calculating said stimulation sensitivity at periodic time intervals; and selecting a time interval between a current calculation of said stimulation sensitivity and a next calculation of said stimulation sensitivity dependent on a difference between a currently calculated value of said stimulation sensitivity and an immediately preceding calculated value of said stimulation sensitivity by shortening said time interval as said difference increases and lengthening said time interval as said difference decreases.

7. A method as claimed in claim 6 comprising the additional step of:

normalizing said difference to a time between said currently calculated value of said stimulation sensitivity and said immediately preceding calculated value of said stimulation sensitivity.

8. A method as claimed in claim 6 wherein the step of delivering stimulation pulses to said biological tissue is further defined by the step of delivering a plurality of successive stimulation pulses to said biological tissue between each calculation of said sensitivity having an energy corresponding to the currently calculated value of the stimulation sensitivity, plus a safety margin.

9. A method as claimed in claim 6 wherein the step of delivering stimulation pulses is further defined by the steps of:

delivering biphasic stimulation pulses for the calculation of said stimulation sensitivity; and delivering monophasic stimulation pulses between each calculation of said sensitivity.

10. A method as claimed in claim 9 wherein the step of delivering biphasic stimulation pulses is further defined by the step of delivering two sub-pulses of opposite polarity with a pause between said two sub-pulses.

* * * * *